(12) United States Patent
Patel (10) Patent No.: US 8,471,176 B2
(45) Date of Patent: Jun. 25, 2013

(54) LASER MACHINE FOR EXAMINATION, PLANNING AND MARKING RAW DIAMOND

(76) Inventor: Arvindbhai L. Patel, Gujarat (IN)

( * ) Notice: Subject to any disclaimer, the term of this patent is extended or adjusted under 35 U.S.C. 154(b) by 780 days.

(21) Appl. No.: 10/490,542

(22) PCT Filed: Oct. 1, 2002

(86) PCT No.: PCT/IN02/00198
§ 371 (c)(1),
(2), (4) Date: Mar. 23, 2004

(87) PCT Pub. No.: WO03/068471
PCT Pub. Date: Aug. 21, 2003

(65) Prior Publication Data
US 2004/0200814 A1 Oct. 14, 2004

(30) Foreign Application Priority Data
Feb. 13, 2002 (IN) ............ 129/MUM/2002

(51) Int. Cl.
 *B23K 26/00* (2006.01)
(52) U.S. Cl.
 USPC .......... 219/121.68; 219/121.67; 219/121.73
(58) Field of Classification Search
 USPC .......... 219/121.68, 121.67, 121.73, 121.82, 219/121.83
 See application file for complete search history.

(56) References Cited

U.S. PATENT DOCUMENTS

| | | | | |
|---|---|---|---|---|
| 2,351,134 A | * | 6/1944 | Koulish | ............ 125/30 |
| 2,382,256 A | * | 8/1945 | Radu | ............... 51/55 |
| 2,384,253 A | * | 9/1945 | Jearum | ............ 51/120 |
| 2,423,777 A | * | 7/1947 | Jearum | ............ 51/234 |
| 2,484,253 A | * | 10/1949 | Spira | ........ 125/30.01 |
| 4,425,900 A | * | 1/1984 | Bosschaert | ...... 125/30.01 |
| 4,529,305 A | | 7/1985 | Welford et al. | |

(Continued)

FOREIGN PATENT DOCUMENTS

| | | |
|---|---|---|
| EP | 1474273 | 11/2004 |
| GB | 2081439 | 2/1982 |

(Continued)

OTHER PUBLICATIONS

German Patent Application DE 4011821, Schneider Werk Graphische Masc, Oct. 17, 1991, "Programme-Controlled Paper Cutting Machine—Optically Scans Cutting Marks Allowing Programming of Cutter Movement".

(Continued)

*Primary Examiner* — M. Alexandra Elve
(74) *Attorney, Agent, or Firm* — Shaukat A. Karjeker; Colin P. Cahoon; Carstens & Cahoon, LLP (57) ABSTRACT

Because of extreme hardness, diamonds have a number of important industrial applications. Generally experts work on it. Experts do marking after examining each rough diamond to decide how it should be cut to yield the greatest value. But in this process, there can be lots of wastage as it is only an image of the stone in the mind of the person. The present invention comprises Laser planner which scans each and every point of diamond by rotating it 360° and thus gives individual coordinate of that diamond. It shows us the wire frame image on the computer monitor. is a machine to scan the stone and to plan and mark for the best-fit diamond from that stone. All the data of the diamond is stored in the computer. It is material saving, time saving, mass processing increase in productivity.

8 Claims, 12 Drawing Sheets

U.S. PATENT DOCUMENTS

| | | | | |
|---|---|---|---|---|
| 4,601,415 A | * | 7/1986 | Koffron | 222/597 |
| 5,190,024 A | * | 3/1993 | Senanayake | 125/30.01 |
| 5,504,303 A | * | 4/1996 | Nagy | 219/121.68 |
| 5,615,005 A | * | 3/1997 | Valente et al. | 356/30 |
| 5,966,673 A | * | 10/1999 | Shannon, Sr. | 702/35 |
| 6,020,954 A | * | 2/2000 | Aggarwal | 356/30 |
| 6,476,351 B1 | * | 11/2002 | Kaplan et al. | 219/121.69 |

FOREIGN PATENT DOCUMENTS

| | | | |
|---|---|---|---|
| GB | 2159636 | | 12/1985 |
| GB | 2159636 A | * | 12/1985 |
| WO | WO 99/61890 | | 12/1989 |
| WO | WO 99/61890 | | 12/1999 |

OTHER PUBLICATIONS

International Publication No. WO/2003/068471 A1, Patel, Arvindbhai L., Aug. 21, 2003, "Laser Machine for Examination, Planning, and Marking Raw Diamond".

International Publication No. WO/1986/006576, Schonstein, et al., Nov. 20, 1986, "Method and Apparatus for Dividing Plant Materials".

PCT International Preliminary Examination for PATEL, Arvindbhai, Int'l Application No. PCT/IN02/00198, Filed Oct. 1, 2002, Jul. 20, 2004.

* cited by examiner

LASER MACHINE FOR EXAMINATION, PLANNING AND MARKING RAW DIAMOND

The application disclosed herein corresponds to International Application No. PCT/IN02/00198, filed on Oct. 1, 2002, which claims priority of Indian Application No. 129/MUM/2002, filed on Feb. 13, 2002, the contents of which are incorporated into this application.

FIELD OF THE INVENTION

The present invention "LASER MACHINE FOR EXAMINATION, PLANNING AND MARKING RAW DIAMOND" More particularly, the present invention relates to a system and method for the plan, cut and mark of diamonds, with material saving, time saving, mass processing increase in productivity of diamond.

Diamond is a mineral composed of pure carbon. It is the hardest naturally occurring substance and popular gemstone. Because of extreme hardness, diamonds have a number of important industrial application. Diamond is a special form of Carbon like Graphite. In the mine, a raw diamond looks like a piece of coal—natural stone. Jewelry grade diamond cutting is a separate and special branch involves marking, cleaving, kerfing, blocking, sawing, bruiting, faceting and polishing.

Inside the raw stone there can be some impurities. The impurities inside the diamond are called NATS and GERUMS. Nats are impurities in the form of particles other then carbon and Gerums are the impurities in the form of micro-cracks in the stone. So, these impurities have to be removed from the stone, and that is why the raw stone is cut in such a way that the maximum carat weight (volume) can be gained.

Before cutting the raw stone it is planned in the mind by imagination from where to cut to yield the desired value and size. Marking is done on the stone for cutting accordingly. To make this decision, the shape of rough diamond and the number and location of impurities is required to be considered as it affects reflectivity and clarity of the diamond. But the human imagination of the mankind can not judge the proper place of the impurities and it may create an error during cutting which may results into wastage. While cutting the stone there are permutation and combination in the form of size and numbers from one stone. When the cutting is done according to the human imagination, the desired proportion of and numbers can not be obtained and there may be a heavy loss.

To come out of this loss present invention provides LASER MACHINE FOR EXAMINATION, PLANNING AND MARKING RAW DIAMOND.

DISCLOSURE OF THE INVENTION

According to state of art optical planner scanning is accomplished in three steps:
1. diamond mapping
2. defining sawing plane
3. pen or laser marking First, light falls on diamond and distance can be measured from the reflection of that light. In this present invention, the three dimensional representation is provided by providing two stereo-pair representations of the finished stone, which are arranged such that when they are viewed binoculary, the operator sees a three-dimensional representation of the finished stone. Then it detects edges of diamond with rotation of the full circle i.e. 360°. After edges detection, The three dimensional representation is provided as an image using optical system, which is provided by electronically and the size of the three-dimensional representation relative to the unfinished stone or image thereof is altered during the examination.

Whereas the present invention comprises Laser planner which scans each and every point of diamond by rotating it 360° and thus gives individual coordinate of that diamond. It shows the wire frame image on the computer monitor.

Laser planner of the present invention contains:
1. laser scanning device
2. 3-D scanning system by using laser with 3-D position in form of wire frame
3. specific die
4. marking device
5. software for finding out the weight of diamond in carat and fitting appropriate biggest size diamond in raw diamond.
6. Electronic assembly The above laser planer system is working with the help of laser scanning device, 3D scanning system, specific die, marking device & electronic assembly wherein 3D scanning system comprising of main body (1), two linear motion blocks (18), two rails (19 & 26), slider (6), nut housing (3), ball screw assembly (17), sensor flag (10), check nuts (8 & 9), die (28) die holder (25), main ball bearing unit (2), bearing (16), spacer (11), motot bracket (12) flexible shaft coupling (15), two stepper/servo motor (13 & 14), wherein electronic assembly comprising two drive card PCBs unit (20 & 21) and body mounting holder (4), wherein marking portion comprising inkpot, pen & wire frame.

The present invention will be described with a preferred embodiment and to see how it may be carried out in practice, with reference to the following drawings of which.

TECHNICAL DETAILS

As FIGS. 1, 2, 3 and 4, on main body 1 two rails 19 and 26 are mounted. Rails 19 and 26 are to define the path of movement. On the rails 19 and 26, two linear motion blocks 18 are mounted. linear motion blocks 18 are to give very less friction in the vertical movement. linear motion blocks 18 are attached with a slider 6 through nut-housing 3, which is fitted on the nut of ball screw assembly 17. The ball screw assembly 17 is of very high accuracy and precise ground and hardened and given exact movement as per command. This ball screw assembly 17 is fitted in the center between two rails 19 and 26. A slider 6 is fitted on the top face of the nut-housing 3 and on the top face of two linear motion blocks 18. The slider 6 is also attached with the sensor flag 10 which assures the home limit position of vertical movement of the slider 6. Slider 6 will move up and down as per the revolution of ball screw 17. To hold the ball screw 17, a main ball bearing 2 is fitted. Two bearings 16 are fitted in the ball bearing unit 2, a check nut 8 is used to restrict the axial movement. Assembly of main ball bearing unit 2 is with two check nuts 8 and 9 and spacer 11. A spacer 11 is put between bearing 16 and check nuts 8 and 9. One check nut 8 is for preventing axial movement of ball screw 17 and another check nut 9 is used to fix the location of bearing 16 in main bearing housing 2. A motor bracket 12 is fitted into the main ball bearing unit 2. A motor 14 is attached on this motor bracket unit 12. A flexible shaft coupling 15 is used to connect the both shaft ends i.e. ball screw shaft 23 and motor shaft 24.

A motor 13 gives the rotation movement to the ball screw 17 without backlash through coupling 15. This rotational movement is converted into linear movement through the ball screw 17, linear motion block 18, slider 6 and nut-housing assembly 3. Scanner 27 and light source are placed in such a way that light falls on stone placed on die 28. The three dimensional representation is rotated relative to the unfinished stone or image thereof during the examination. The rotation is effected about three mutually perpendicular axes. During the examination, the unfinished stone or image thereof is rotated about an substantially different from the axis of viewing and 3D representation is rotated in a synchronous manner. The scanner 27 is attached with computer so that after scanning the raw stone structure and physical data of the stone can be seen on the screen of the computer. Physical data of the stone is counted by the computer program installed in the computer.

Two stepper/servo (13 and 14) motors are used in this machine. One is for vertical movement whereas other is for rotary axis and ling. In the rotary axis unit, there is a double shaft motor. Rotary axis unit is fitted by means of right angle aluminum bracket. On the top shaft, a die holder unit 25 is fitted by means of right angle aluminum bracket whereas dedicated encoder dish is fitted for precise reference of home position.

In the electronic assembly two PCBs 20 and 21 are used. One PCB 21 is isolation PCB and the other PCB 20 as control unit. PCBs are placed on PCB holder 22. The entire unit is placed on the body mounting bracket 4. A specifically designed die is fitted on the die holder carrying a diamond which is to be planned/shaped. This is very dedicated die and purposefully designed for this exclusive application. This die is having one reference notch which is always ensuring a position in die holder.

A diamond can be fixed on top of the die by either hard glue or stitching by double side insulation tape. The pen is used to mark girdle, facet and table on the surface of diamond. Noticeable feature is servo controlled PWM (Pulse Width Modulation) pen actuator, which controls the marking action.

Power supply is connected to Drive card PCB. Drive card consists of four identical drive circuit through which it drives the two motors for vertical and rotary movement of the assembly. Another two units are related to marker—one controls the relay coils of marker while another one manages pump to control the flow of ink. Opto-isolation PCB uses opto-couplers to protect the planner unit from any short circuit occurred inside the computer and vice versa. Home limit determines the motion of the assembly.
PCB senses and gives pre-defined movement of the planner unit. After scanning one diamond when next diamond is placed PCB provides zero reference to start scanning of new diamond.

Figure 1:
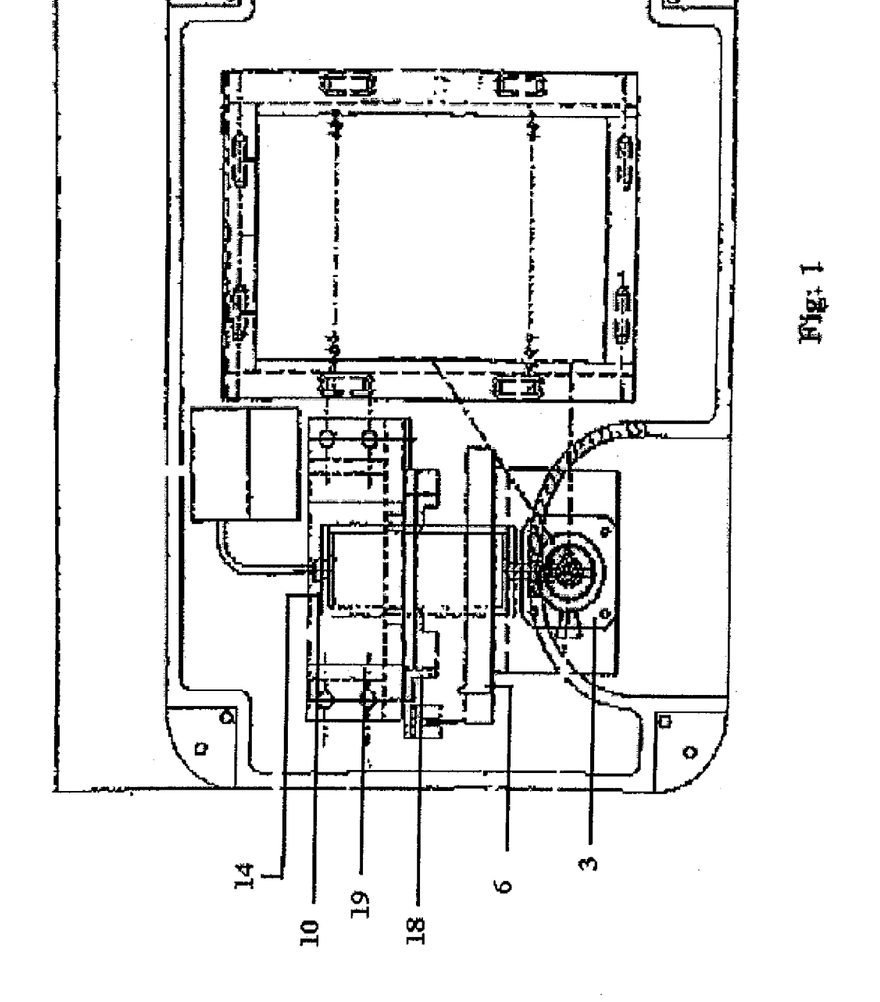
FIG. 1. represents a block diagram of the machine
FIG. 2. represents side view of the machine
FIG. 3. represents top view of the machine
FIG. 4. represents front view of the machine
FIG. 5. represents block diagram of side view of the machine
FIG. 6. represents block diagram of top view of the machine
FIG. 7. represents block diagram of front view of the machine
FIG. 8. represents a chart of the machine
FIG. 9. represents a drawing showing movements of the axis.
Figure 2:
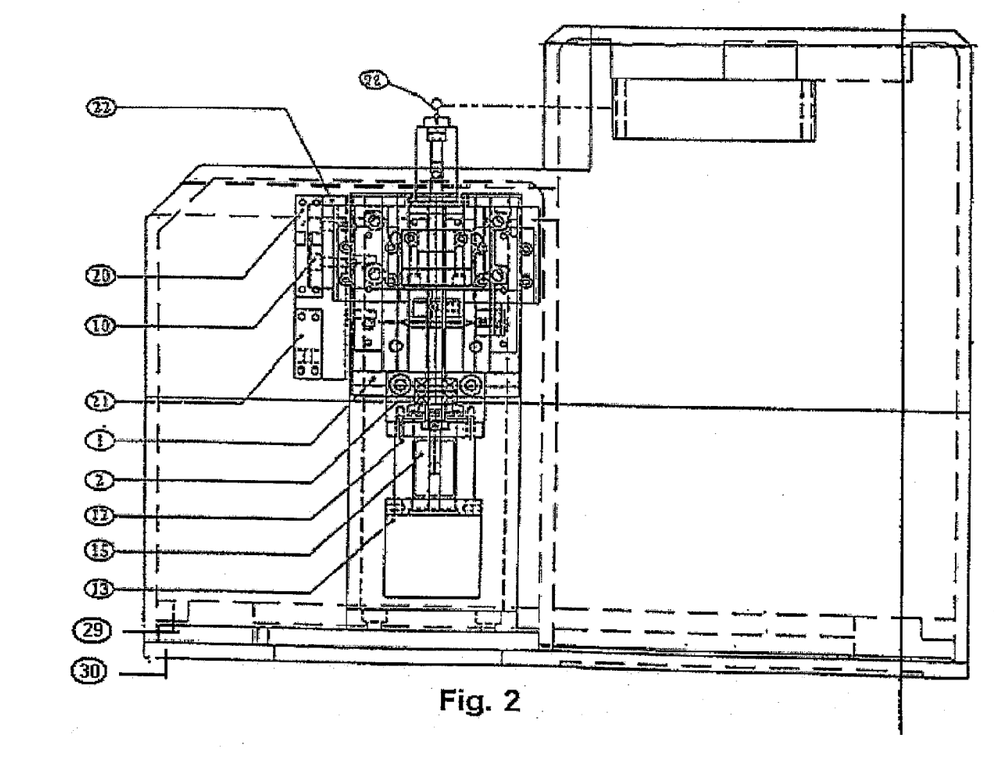
Figure 3:
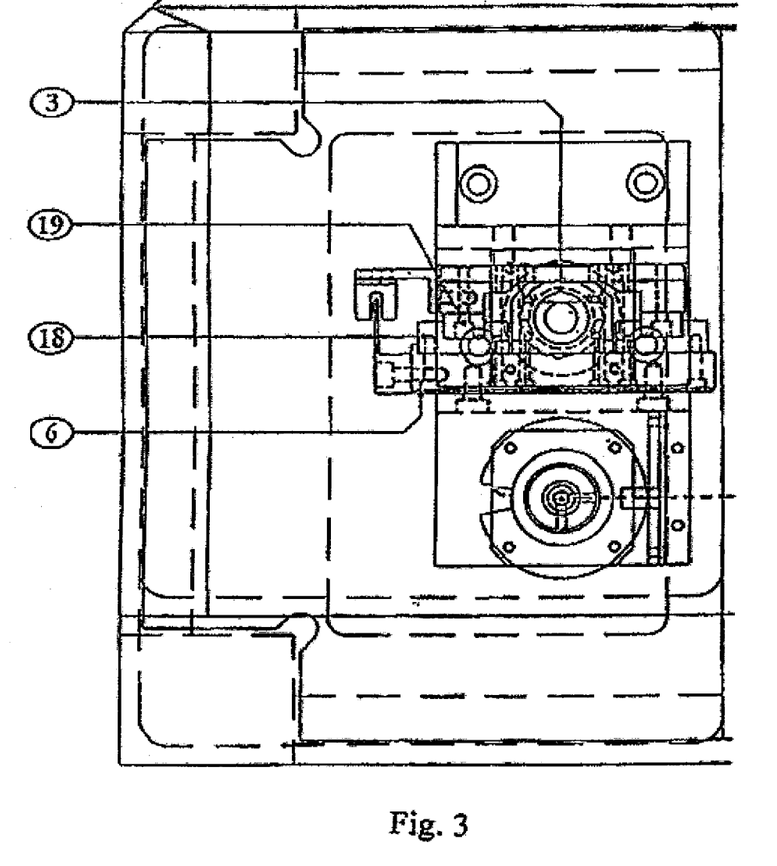
Figure 4:
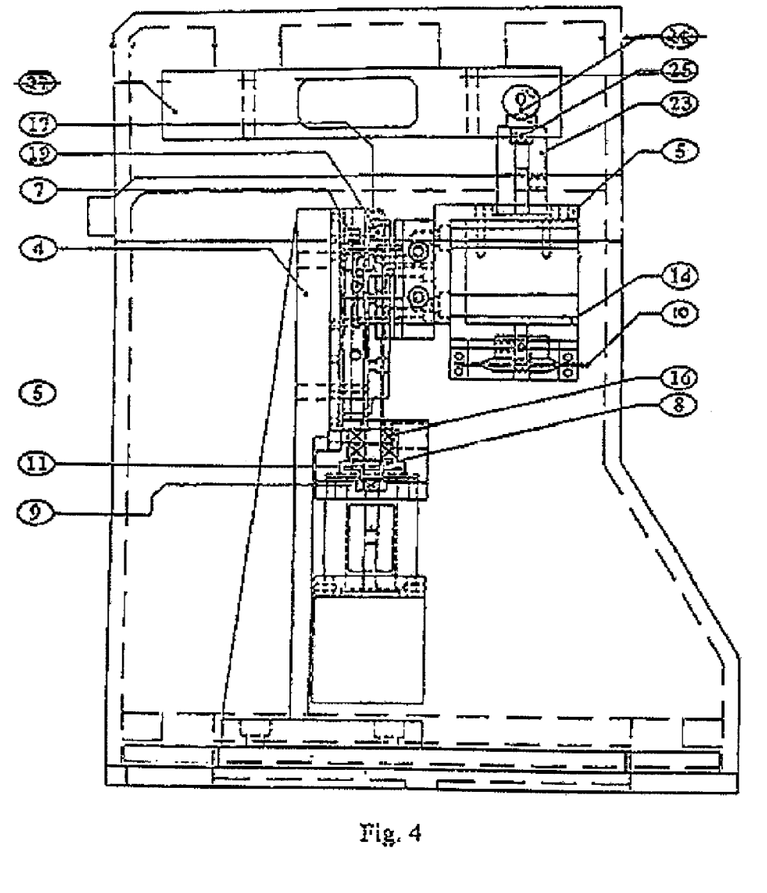
Figure 5:
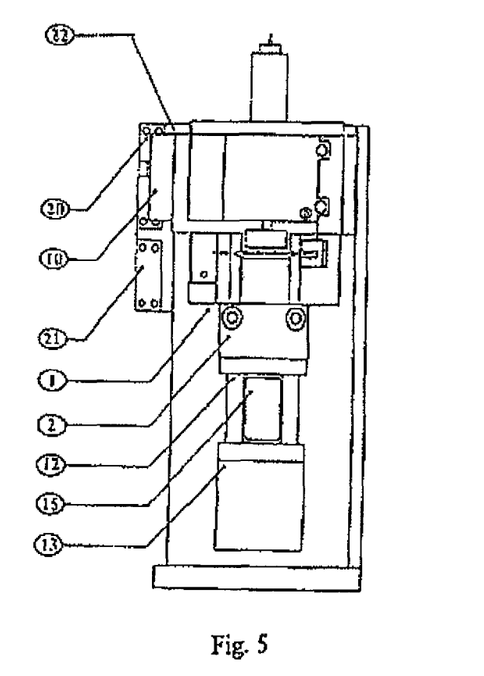
Figure 6:
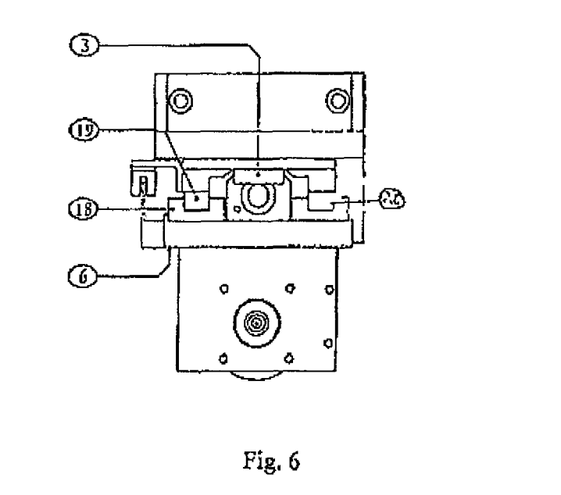
Figure 7:
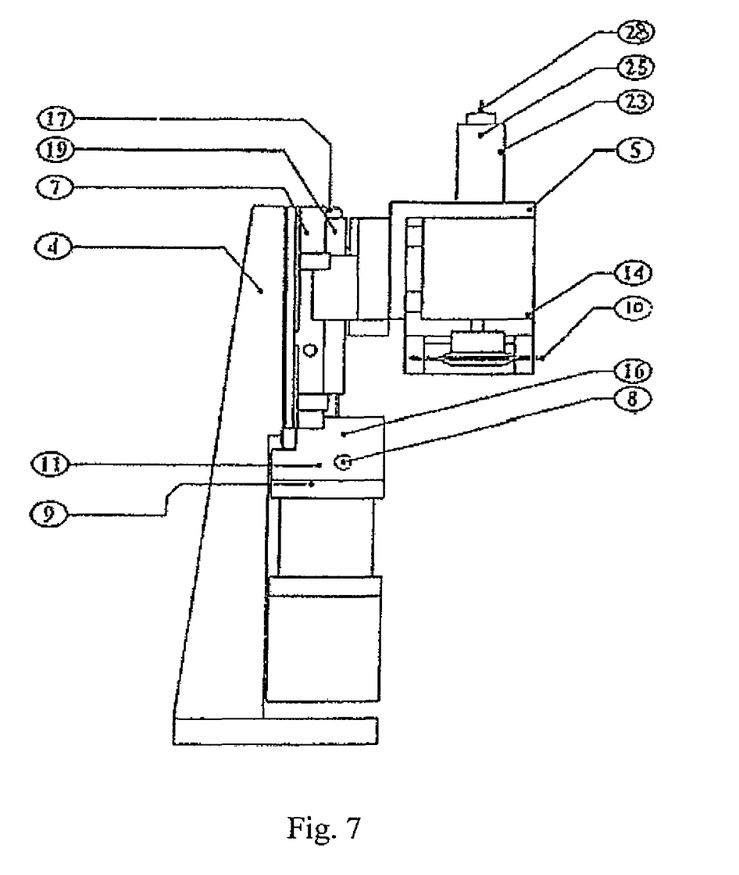
Figure 8:
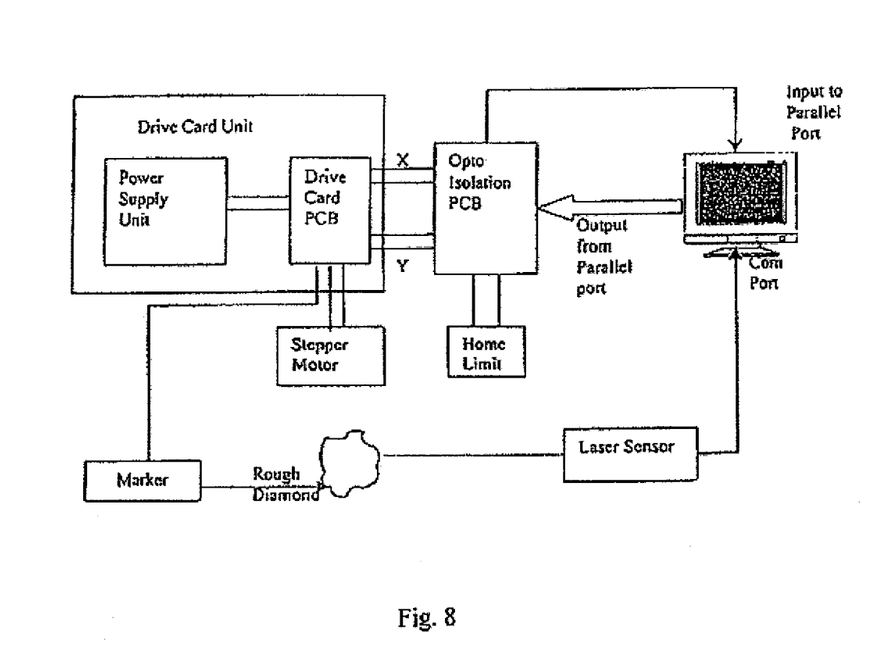
Figure 9:
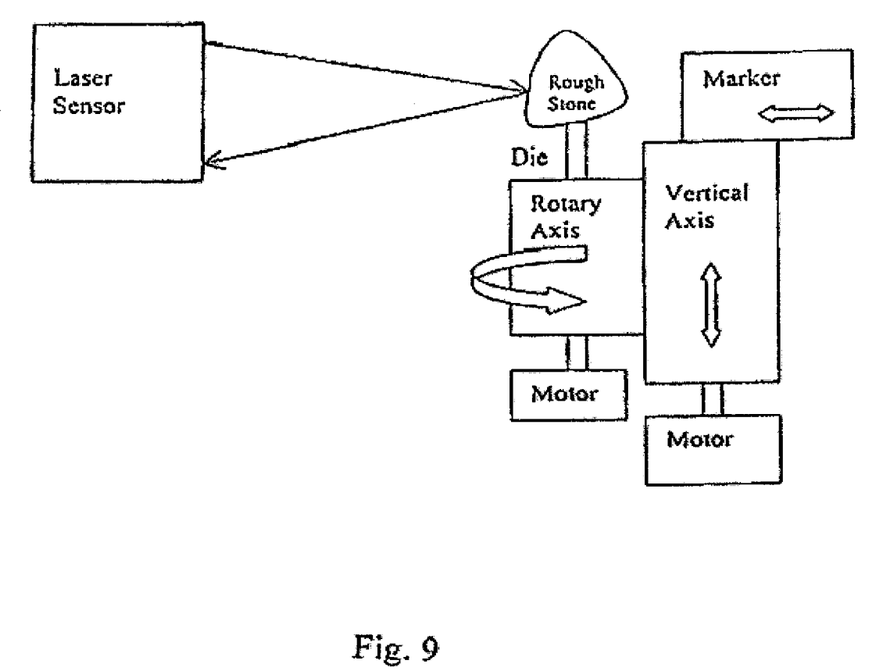
Figure 10:
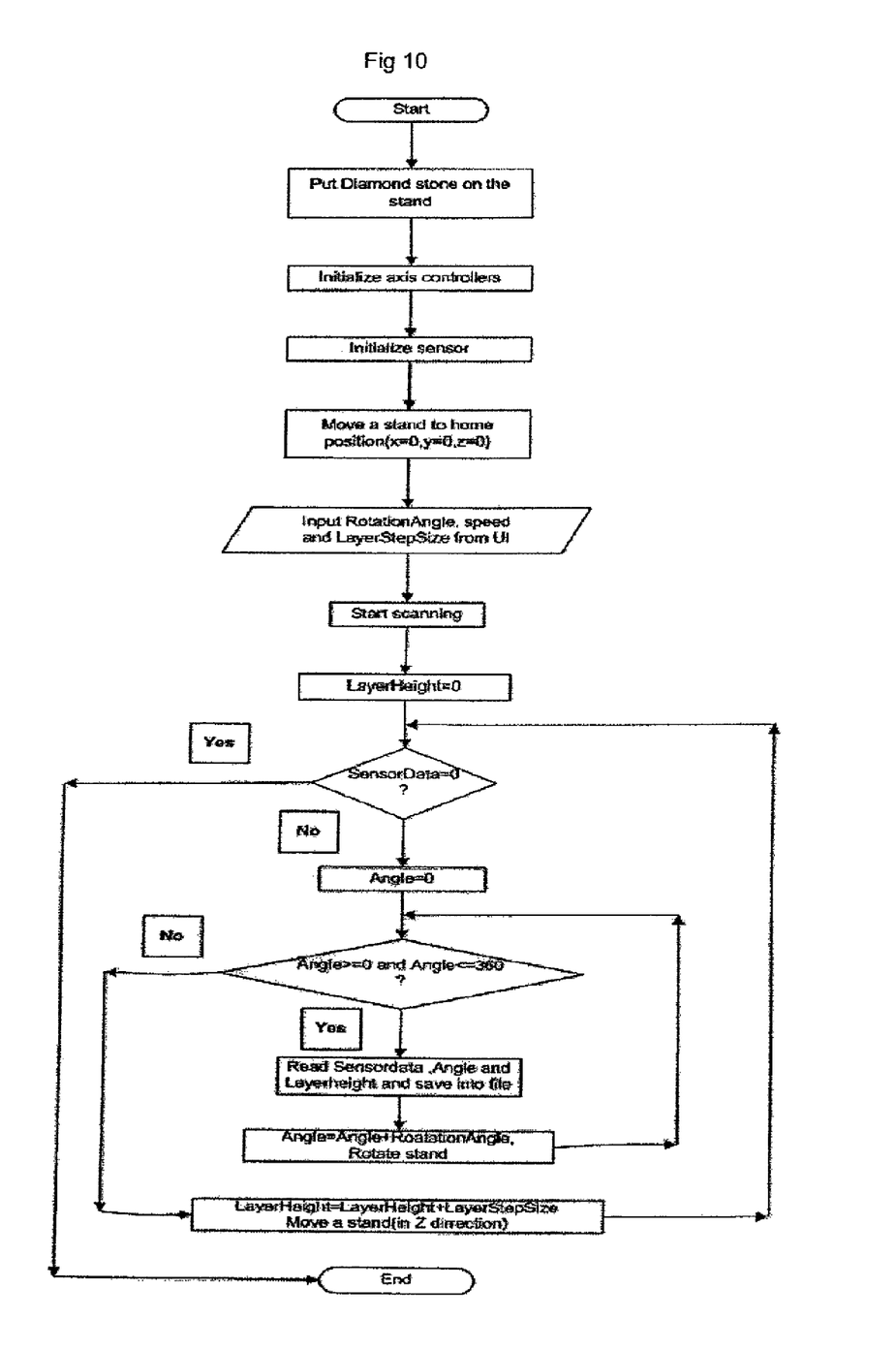
FIG. 10. represents a flow chart of scanning module
FIG. 11. represents a die and die holder (28 and 25)
Figure 12:
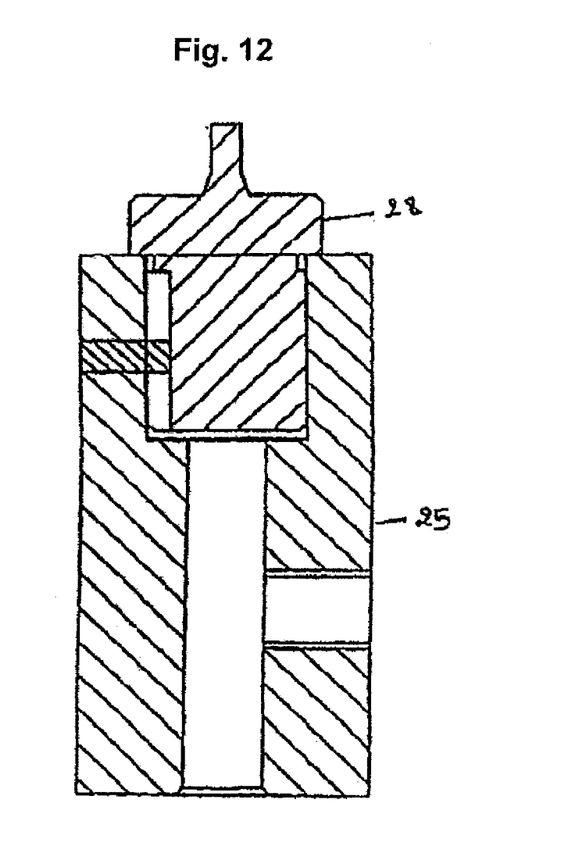
FIG. 12 represents a sensor flag (11)
FIG. 13. represents a check nuts (8 & 9)
FIG. 14. represents a slider (6)
FIG. 15. represents a nut housing (3)
Figure 13:
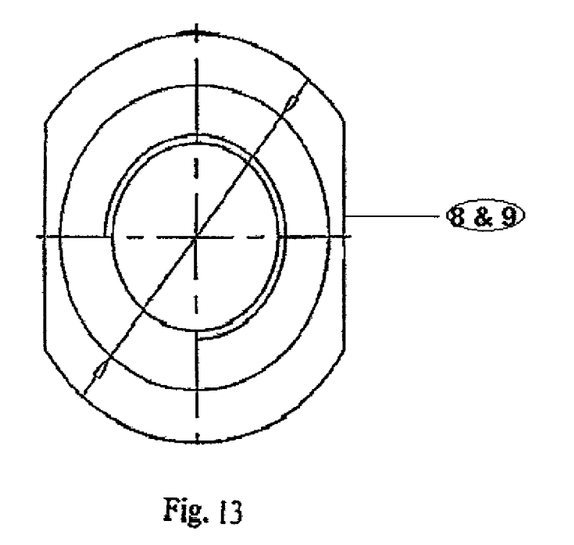
Figure 14:
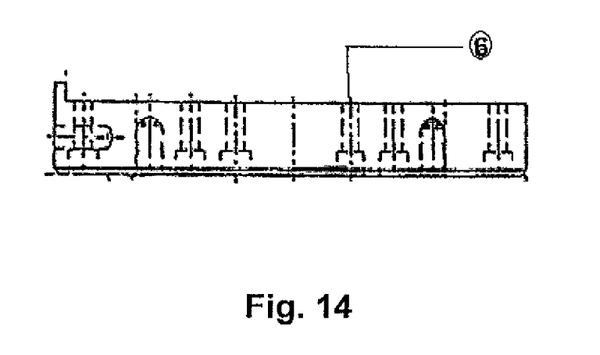

In the present invention the design of the die is very important. Die is having a small hole of 1 mm diameter. Die is to be fitted on die holder through pin, which is connected with upper shaft of the motor. Inside the upper gap of the die holder spacer is press fitted and inside the spacer a pin is press fitted. Upper 1 mm distance of the pin is left to fit the die in an easy and smooth manner. A stone is put on the die with the help of glue. The sensor senses the distance by vertical movement of the assembly the vertical movement of the die with stone occurs due to the vertical movement of slider. The stone is being rotated through rotary axis. The die moves vertically upward and it is under control of mechanical stopper. By all these movement and with the help of computer program the structural data of the diamond is stored in the computer. This, as a whole is a scanning module. Diamond is put on the stand of the die. Now sensor will be initialized so that stand will move to home position where all the axis are at zero. Rotation angle of the diamond with speed and layer step size has to be provided through user interface. The scanning starts from zero$^{th}$ layer i.e. layer height is zero. All the data of the diamond is saved in a file, then again angle is changed by rotating the diamond stand all the process repeats. When rotating unit completes one revolution, the vertical unit moves up by one step. Scanning continue till the stone surface ends or the die material is sensed by sensor. Thus structural data is being collected for one rotary motion, then specific increment in vertical step and as a result combines 3D image of the rough stone.

Marking portion of the machine contains a pump along with inkpot. Inkpot is connected to the pen by a hollow tube for smooth supply of ink. Pump is controlled by a relay. When relay gets signal from drive card in the form of high voltage pulse, it gets magnetized and becomes activated and so it presses the marker pen to touch and mark the stone.

Then stone will be marked w.r.t. facet, table and girdles. According to presence of nats and gerums, once again planes have to be judged and volume+mass will be calculated. Again marking is to be done and then again to find out planes. As a result, optimized diamond is got.

Wire frame concept is used to display the object. Using concept of volume of tetrahedron, mass can be calculated. Also a computer program is used for finding out the weight of diamond in carat and fitting appropriate biggest size diamond in raw diamond. The Laser planner determines "best-fit" diamond from the rough stone with consideration of maximum mass and volume. It should be clear to a person skilled in the art that many modifications and variations of the present invention are possible concerning the design of the diamond with EXAMINATION, PLANNING AND MARKING RAW DIAMOND and as well as of the method of laser planer on diamonds, in the framework of their definitions in the claims.

The invention claimed is:

1. An apparatus for examining and marking a raw diamond, comprising:
   (a) a die for holding the raw diamond;
   (b) a first servo motor for moving said die vertically;
   (c) a second servo motor for rotating said die axially;
   (d) a laser scanner that maps the surface coordinates of the raw diamond as the die is rotated through 360 degrees by said second servo motor and progressively moved vertically by said first servo motor after each rotation;
   (e) a computer that controls the movement of the first and second servo motors and produces a three-dimensional image of said raw diamond based on the surface coordinates mapped by the laser scanner;
   (f) a software program in said computer that calculates the mass and weight of the diamond and calculates a best fit cut that maximizes the size of a cut diamond within the constraints of the mass and the volume of the raw diamond as determined by the laser scanner; and (g) a marking device controlled by said computer that marks cutting points on the surface of the raw diamond according to said calculated best fit cut.

2. The apparatus according to claim 1, wherein the die is mounted onto a die holder, wherein the die holder has a protruding pin that inserts into a hole in the bottom of the die and wherein the die has a reference notch to ensure proper position on the die holder.

3. The apparatus according to claim 1, wherein the marking device marks girdle, facets, and table on the surface of the raw diamond.

4. The apparatus according to claim 1, wherein the marking device comprises:
   a pen;
   an inkpot that supplies ink to the pen via a hollow tube;
   a pump that pumps ink from the inkpot to the pen;
   a servo controlled pen actuator that moves the pen; and
   a drive circuit that controls the pump.

5. The apparatus according to claim 1, further comprising an opto-isolation printed circuit board that uses opto-couplers to protect the laser scanner from short circuits inside the computer and vice versa.

6. The apparatus according to claim 1, wherein the software program in the computer uses the three-dimensional image to calculate the mass of the raw diamond according to the concept of volume of tetrahedron.

7. The apparatus according to claim 1, further comprising:
   two vertical rails;
   two motion blocks that move along said rails;
   a ball screw assembly positioned between the vertical rails;
   a ball bearing unit fitted to said ball screw assembly;
   a nut housing fitted on the ball screw assembly; and
   a slider coupled to said motion blocks and nut housing, wherein the die is coupled to the slider and wherein vertical movement of the slider is produced by rotation of the ball screw assembly via said first servo motor.

8. The apparatus according to claim 7, wherein said second servo motor is coupled to the ball bearing unit via a motor bracket unit.

* * * * *